US005525473A

United States Patent [19]
Hill et al.

[11] Patent Number: 5,525,473
[45] Date of Patent: Jun. 11, 1996

[54] ASSAY FOR BONE ALKALINE PHOSPHATASE

[75] Inventors: Craig S. Hill, Encinitas; Robert L. Wolfert, San Diego, both of Calif.

[73] Assignee: Hybritech Incorporated, San Diego, Calif.

[21] Appl. No.: 239,185

[22] Filed: May 5, 1994

Related U.S. Application Data

[63] Continuation of Ser. No. 850,013, Mar. 10, 1992, abandoned, which is a continuation of Ser. No. 304,521, Jan. 31, 1989, abandoned.

[51] Int. Cl.⁶ .................................................. G01N 33/573
[52] U.S. Cl. ..................... 435/7.4; 435/7.94; 435/21; 435/975; 436/518; 436/548; 436/808; 530/388.26; 530/391.1; 530/391.3
[58] Field of Search ................................. 435/7.4, 7.92, 435/7.94, 7.95, 21, 975; 436/518, 804, 548, 808; 530/388.26, 391.1, 391.3

[56] References Cited

U.S. PATENT DOCUMENTS

| | | | |
|---|---|---|---|
| 4,302,536 | 11/1981 | Longenecker | 435/7.4 |
| 4,376,110 | 3/1988 | David et al. | 436/513 |
| 4,740,468 | 4/1988 | Weng et al. | 435/7 |
| 4,912,033 | 3/1990 | Ladenson et al. | 435/7 |
| 4,916,056 | 4/1990 | Brown, III et al. | 435/7 |
| 5,087,573 | 2/1992 | Anderson et al. | 435/240 |

FOREIGN PATENT DOCUMENTS 3420926  12/1985  Germany .

OTHER PUBLICATIONS

Singh and Tsang, "An In Vitro Production of Bone Specific Alkaline Phosphatase" *Experimental Cell Research.* 95:347–358 (1975).

Masuhara et al., "Purification Of Bone Alkaline Phosphatase From Human Osteosarcoma" *Bone and Mineral.* 3:159–170 (1987)

Bailyes et al., "The Preparation Of Monoclonal Antibodies To Human Bone and Liver Alkaline Phosphatase And Their Use In Immunoaffinity Purification And In Studying These Enzyme When Present In Serum" *Biochemistry Journal* vol. 244:725–733 (1987).

Nerurkar et al., "Rapid Detection Of Herpes Simplex Virus In Clinical Specimens By Use Of A Capture Biotin–Streptavidin Enzyme–Linked Immunosorbet Assay" *Journal of Clinical Microbiology.* vol. 20, No.1:109–114 (1984).

Seabrook et al., "The Distinction Of Bone And Liver Isoenzyme Of Alkaline Phosphatase In Serum Using A Monoclonal Antibody" *Clinica Chimica Acta.* 172:261–266 (1988).

Lawson et al.,"Isolation And Preliminary Characterization Of A Monoclonal Antibody That Interacts Perferentially With The Liever Isoenzyme Of Human Alkaline" *Clin. Chem.* vol. 31 No. 3:381–385 (1985).

*Primary Examiner*—Toni R. Scheiner
*Assistant Examiner*—Susan C. Wolski
*Attorney, Agent, or Firm*—Campbell and Flores

[57] ABSTRACT

Monoclonal antibodies highly specific for human bone alkaline phosphatase, especially in the presence of human liver alkaline phosphatase, and their use in assays for human bone alkaline phosphatase are disclosed. A kit using the antibodies in an assay for human bone alkaline phosphatase is also disclosed.

37 Claims, 9 Drawing Sheets

Patient Sera—BA1F 419 and BA1B 067

Patient Sera—BA1F 419 and BA1G 121

Patient Sera—BA1F 419 and BA1G 339

ASSAY FOR BONE ALKALINE PHOSPHATASE

This application is a continuation of application Ser. No. 07/850,013, filed Mar. 10, 1992, now abandoned, which in turn is a continuation of application Ser. No. 07/304,521, filed Jan. 31, 1989, now abandoned.

BACKGROUND OF THE INVENTION

The present invention is method for detecting the presence and concentration of bone alkaline phosphatase (BAP) in human body fluids. Elevated BAP levels in serum is symptomatic for serious disorders such as bone metastasis from carcinomas, such as those of the breast and prostate, and Paget's disease (osteitis deformous).

Paget's disease is a serious disease affecting primarily those over the age of 40. The disease is slowly progressive, first involving bone resorption followed by a distorted pattern of new growth in bones such as the pelvis, femur, skull, tibia, vertebrae, clavicle and humerus. The disease exhibits gross symptoms such as bowing of the tibia or femur, enlargement of the skull, shortened stature, and severe aching in the affected bones. Neural effects may include deafness or spinal cord compression accompanied by paresis or paraplegia.

Until now the only reliable diagnosis for Paget's disease has been by x-ray examination. Routine assays for serum BAP are confined to measuring total alkaline phosphatase concentration. Several related forms of alkaline phosphatase exist in the serum, specifically those of the intestinal, placental and the hepatic/renal/skeletal groups. These three broad groups C an usually be separated using the time-consuming procedure of electro-phoretic assay, but until now assays for distinguishing between the clinically important markers of bone and liver alkaline phosphatases (LAP) were at best ambiguous and time-consuming. The present invention is directed to a convenient highly specific sandwich immunoassay method for determining the presence or concentration of BAP and especially so in the presence of LAP.

SUMMARY OF THE INVENTION

The present invention is directed to forward, reverse and simultaneous sandwich assays for the presence or concentration of human bone alkaline phosphatase ("BAP") using monoclonal antibodies that are highly specific for BAP, especially in the presence of human liver alkaline phosphatase ("LAP"), as set forth below in the Detailed Description of the Invention. Another aspect of the invention are monoclonal antibodies that are highly specific for BAP, and especially in the presence of LAP, as described below in the Detailed Description. Yet another aspect of the invention is a kit for detecting the presence or concentration of BAP, comprising a monoclonal antibody for BAP which is bound or could be bound to a solid support, a labelled monoclonal antibody for BAP, and a signal generating substance if required, wherein both monoclonal antibodies are highly specific for BAP, especially in the presence of LAP, as discussed below in the Detailed Description.

DETAILED DESCRIPTION

Figure 1:
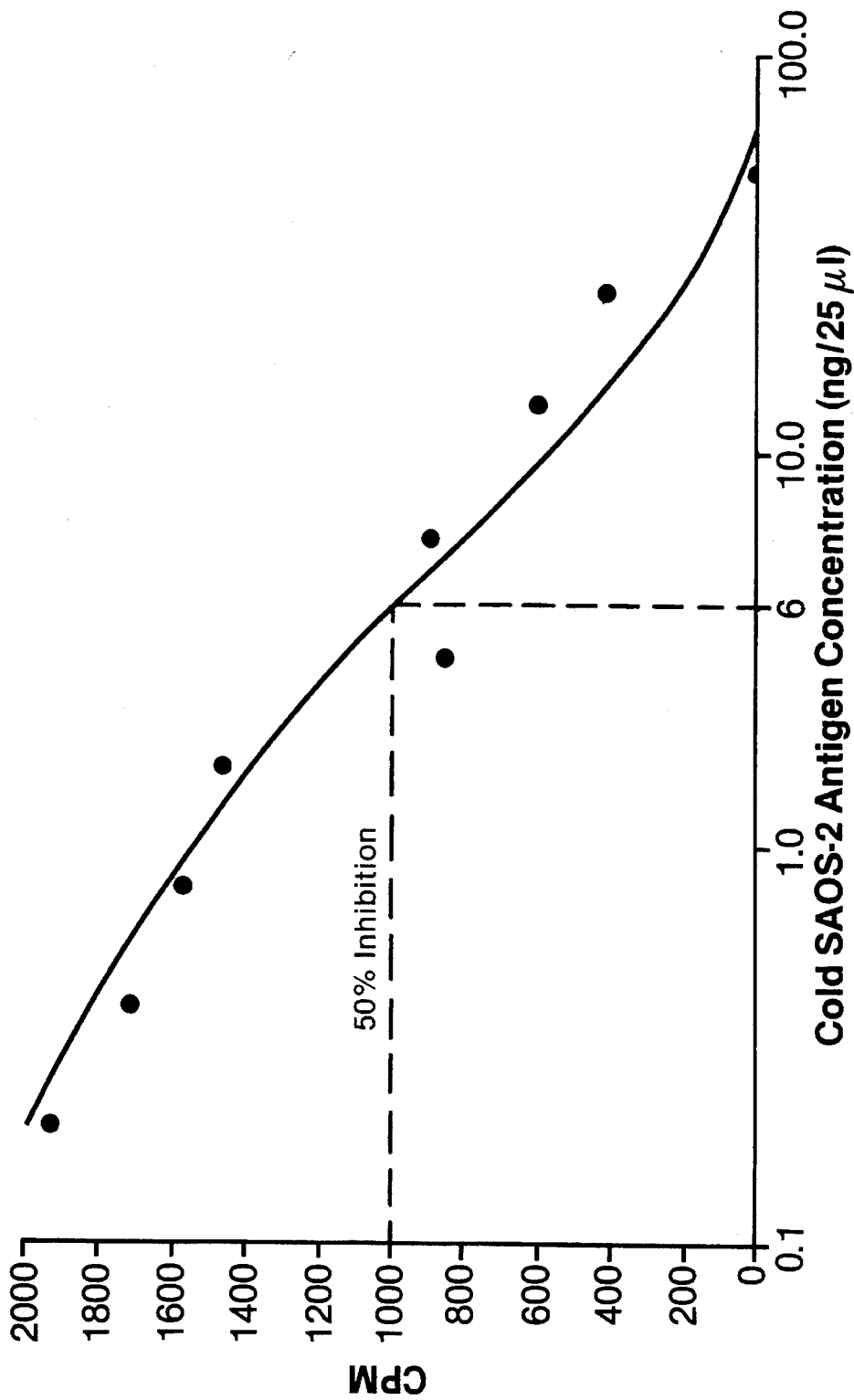
FIG. 1 depicts the simultaneous saturation analysis of monoclonal antibody BA1G 121 using radiolabelled, BAP and crude, unlabelled BAP.

The present invention is directed to a sandwich assay highly specific for BAP in the presence of LAP and other human alkaline phosphatase isoenzymes. (The concept of a sandwich assay in general is described in David et al., U.S. Pat. Nos. 4,376,110 and 4,486,530, issued Mar. 8, 1983 and Dec. 4, 1984, respectively, herein incorporated by reference.) The invention also encompasses monoclonal antibodies highly specific for BAP, especially so in the presence of LAP.

Specifically, one embodiment of the invention is a "forward" assay that entails a process for the determination of the presence of or concentration of BAP in a fluid comprising the steps of:

(a) contacting a sample of the fluid with a first monoclonal antibody for BAP, wherein the first monoclonal antibody is bound to a solid carrier insoluble in the fluid in order to form an insoluble complex between the first monoclonal antibody and the BAP;

(b) separating the fluid sample containing unreacted BAP from the insoluble complex of the first monoclonal antibody and BAP;

(c) reacting a measured amount of a second, monoclonal antibody to BAP which is labelled and which antibody is soluble in the fluid with the insoluble complex of the first monoclonal antibody and BAP, in order to form an insoluble complex of the first monoclonal antibody, BAP, and second, labeled antibody;

(d) separating the solid carrier from unreacted second, antibody;

(e) measuring either the amount of second, antibody associated with the solid carrier or the amount of unreacted second, antibody;

(f) relating the amount of second antibody measured with the amount of labelled antibody measured for a control sample prepared in accordance with steps (a) through (e), said control sample known to be free of BAP, to determine the presence of BAP in said fluid sample, of relating the amount of labelled antibody measured in said fluid sample with the amount of labelled antibody measured for samples containing known amounts of BAP prepared in accordance with steps (a) through (e) to determine the concentration of BAP in the fluid sample;

wherein both monoclonal antibodies used are highly specific for BAP, especially in the presence of LAP.

Another embodiment of the invention is a "reverse" sandwich assay for BAP that entails a process for the determination of the presence of or concentration of BAP in a fluid comprising the steps:

(a) contacting a sample of the fluid with a measured amount of the first monoclonal antibody for BAP, wherein the first monoclonal antibody is labelled, in order to form a soluble complex between the first monoclonal antibody and BAP:

(b) contacting the sample (which now contains the soluble complex) with a second monoclonal antibody to BAP, which second antibody is bound to a solid carrier insoluble in the fluid, with the soluble complex of the first monoclonal antibody and BAP, in order to form an insoluble complex of the first monoclonal antibody, BAP, and second, antibody;

(c) separating the solid carrier from unreacted first, antibody;

(d) measuring either the amount of first, antibody associated with the solid carrier or the amount of unreacted first, labelled antibody;

(e) relating the amount of first antibody measured with the amount of labelled antibody measured for a control sample prepared in accordance with steps (a) through (d), said control sample being known to be free of BAP, to determine the presence of BAP in said fluid sample, or relating the amount of labelled antibody measured for the fluid sample with the amount of labelled antibody measured for samples containing known amounts of BAP prepared in accordance with steps (a) through (d) to determine the concentration of BAP in the fluid sample;

wherein both monoclonal antibodies used are highly specific for BAP, especially in the presence of LAP.

Yet another aspect of the present invention involves a "simultaneous" assay for BAP that entails a process for the determination of the presence of concentration of BAP enzyme in a fluid comprising the steps:

(a) simultaneously contacting a sample of the fluid with a first and second monoclonal antibodies for BAP, wherein the first monoclonal antibody is bound to a solid carrier insoluble in the fluid and the second monoclonal antibody is labelled and provided in a measured amount, in order to form an insoluble complex between the first monoclonal antibody and BAP;

(b) separating the solid carrier from the fluid sample unreacted second, antibody;

(c) measuring either the amount of second, antibody associated with the solid carrier or the amount of unreacted second, antibodies;

(d) relating the amount of labelled antibody measured with the amount of labelled antibody measured for a control sample prepared in steps (a) through (c), wherein the control sample is known to be free of BAP, to determine the presence of BAP in said sample fluid, or relating the amount of labelled antibody measured for the fluid sample with the amount of labelled antibody measured for samples containing known amounts of BAP prepared in accordance with steps (a) through (c),to determine the concentration of BAP in the fluid sample;

wherein the monoclonal antibodies are both highly specific for BAP, especially in the presence of LAP.

A preferred embodiment of the above forward, reverse or simultaneous assays has the first antibody the product of a cell line different than that of second monoclonal antibody. Another preferred embodiment of the above forward, reverse or simultaneous assays occurs when the first and second monoclonal antibodies are a product of the same cell line. Further preferred embodiments within the above two preferred embodiments described immediately above include assays wherein the labelled antibody is labelled with a radioisotope, an enzyme, biotin, avidin, a chromogenic substance, or a fluorogenic substance. A preferred embodiment of the particular labelling preferred embodiment entails having the monoclonal antibodies chosen from the group consisting of BA1F 419, BA1G 017, BA1G 121, BA1G 151, and BA1G 339. Especially preferred embodiments occur when the BA1F 419, BA1G 017, BA1G 121, BA1G 151, or BA1G 339 monoclonal antibody is labelled with the radioactive isotope $^{125}$I, or when the antibody is labelled with an enzyme other than alkaline phosphatase (e.g., beta-galactosidase, horse radish peroxidase, etc.), or when the antibody is labelled with biotin, and wherein the amount of labelled antibody is measured by adding a measured amount of streptavidinconjugated enzyme label where the enzyme is other than an alkaline phosphatase.

Other preferred embodiments include the above forward, reverse or simultaneous assays, wherein the unlabelled antibody is bound directly or indirectly to a plastic bead to a porous membrane, and especially so when the unlabelled antibody is bound to microparticles, which microparticles are in turn bound to a porous membrane. Similarly, preferred embodiments of the above forward, reverse or simultaneous assays and wherein the labelled antibody is labelled with a radioactive isotope, an enzyme, biotin, avidin, chromogenic substance, or a fluorogenic substance includes embodiments wherein the unlabelled monoclonal antibody is bound directly or indirectly to a porous membrane, and especially so when the unlabeled monoclonal antibody is bound to microparticles, which microparticles are in turn bound to a porous membrane.

When discussing the present invention, various terms have specific connotations. Thus, the term "fluid" means human serum, plasma, whole blood, urine or tumor ascites. The term "solid carrier" means common supports used in immunometric assays made from natural and synthetic material. The support required is insoluble in water and can be rigid or non-rigid. Among such supports are filter paper, filtering devices (e.g., glass membranes), plastic beads (such as polystyrene beads), test tubes or (multiple) test wells made from polyethylene, polystyrene, polypropylene, nylon, nitrocellulose, and glass microfibres. Also useful are particulate materials such as agarose, cross-linked dextran and other polysaccharides. It will be understood to one skilled in the art that for the present assay the capture antibody can first bind to the BAP antigen then bind to the carrier through, for instance, an anti-mouse IgG antibody, an avidin-biotin system, or the like.

Preferred embodiments of the invention have the capture antibody being bound to a porous membrane. By porous membrane we mean flexible or rigid matrix made from any of a variety of filtration or chromatographic materials including glass fibres and micro-fibres and natural or synthetic materials. Fluids should be able to flow into and pass easily through the membrane. The membrane should also preferably have pores of at least 0.1 µ and preferably at least 1.0 µ. The porous membrane can be used by itself or as part of a more elaborate device. Such devices includes the ICON® and like devices described in Valkirs et el., U.S. Pat. Nos. 4,632,901 and 4,727,019, issued Dec. 20, 1986 and Feb. 23, 1988, respectively, herein incorporated by reference. Another such device is the TEST-PAK® device of Abbott Laboratories (North Chicago, Ill.), described in European Patent Application No. 217,403, published Apr. 8, 1987. Still other devices containing the present porous membrane include the device of Bauer et al., U.S. Pat. No. 3,811,840, issued May 21, 1974, Cole et al., U.S. Pat. No. 4,407,943, issued Oct. 4, 1983, Cole et al., U.S. Pat. No. 4,246,339, issued Jan. 20, 1981, Geigel et al., U.S. Pat. No. 4,517,288, issued May 14, 1985, F. S. Intengan, U.S. Pat. No. 4,440,301. issued Apr. 3, 1984, M. E. Jolly, U.S. Pat. No. 4,704,255, issued Nov. 3, 1987, Tom et al., U.S. Pat. No. 4,366.241, issued Dec. 28, 1982, or Weng et al., U.S. Pat. No. 4,740,468, issued Apr. 26, 1988, all of which are herein incorporated by reference.

The capture monoclonal antibody can be directly or indirectly bound to the membrane. The direct binding can be a covalent or non-covalent one by methods well known in the art (for example, the use of glutaraldehyde and aminosilanes). See, for example, "Immobilized Enzymes", Ichiro Chibata, Halstead Press, New York (1978), Cuatrecasas, *J. Bio. Chem.* 245: 3059 (1970), and March et al., *Anal. Biochem.* 60, p149 et seq. (1974). The non-covalent binding takes advantage of the natural adhesion to the non-synthetic and especially the synthetic fibers by antibodies. Thus, appropriately buffered solutions can be mixed with the membrane then evaporated leaving a coating of the desired antibody on the membrane.

The non-direct method for applying the antibody to the membrane employs microparticles which are bound to the membrane, or both matrix of membrane, on the surface of the membrane, or to other particles which are in turn bound to the membrane. The particles can be any shape but preferably spherical. The size of the particles should be such that they do not migrate through the membrane to any significant degree. The size of the particles may vary, but in general they should be slightly larger than the minnimum pore size of the membrane and smaller than the maximum pore size, or in the alternative, should be larger than the maximum pore size. (Thus, the particles can be bound with the matrix of membrane, on the surface of the membrane, or to other particles which are in turn bound to the membrane) The particles can be made up of a variety of naturally occurring or synthetic materials. Exemplary of such particles are those made from polyethylene, polyacrylates, polyacrytamide, or naturally occurring materials such as cross-linked polysaccharides like agarose, dextran, cellulose, starch and the like. The primary requirement is that materials do not contribute a signal, usually light absorption, that would cause the zone in which the particles were located to have a different signal than the rest of the membrane.

The antibody can be covalently or non-covalently bound to the particle. The binding to the particle uses methods similar to those discussed above for binding the antibody directly to the membrane.

The particles are usually applied to the membrane in an area smaller than the surface area of the part of the membrane that it is applied to. Several methods known in the art can be employed. One such method employs various mechanical means (or directly) to apply a suspension, frequently aqueous ("latex") to the membrane.

The methods and use of microparticle for the instant invention are further discussed in Weng el., U.S. Pat. No. 4,740,468, issued Apr. 26, 1988 (see especially columns 13, 14 and 15), Brown et al., European Patent Application No. 217,403, published Apr. 8, 1987, and A. S. Rubenstein, European Patent Application No. 200,381, published Nov. 5, 1986.

The separation steps for the various assay formats (e.g. forward, simultaneous, and reverse) can be performed by methods known in the art. Where indicated, a simple washing with buffer followed by filtration or aspiration is sufficient. After washing, it is sometimes appropriate, as with particulate supports to centrifuge the support, to aspirate the washing liquid, add wash liquid again and aspirate. For membrane and filters, additional washing with buffer may often be sufficient, preferably drawing the liquid through the membrane or filter by applying vacuum to the opposite side of the membrane or filter or contacting the opposite side of the filter or membrane with a liquid absorbing member that draws the liquid through, for instance, by a capillary action.

Moderate temperatures are normally employed for carrying out the assay. Constant temperatures during the period of the measurement are generally required only if the assay is performed without comparison with a control sample. The temperatures for the determination will generally range from about 10° C.–50° C., more usually from abut 15°–45° C.

The concentration of BAP which may be asseyed will generally vary from about $10^{-4}$ to $10^{-10}$ M, more usually from about $10^{-5}$ to $10^{-8}$ M. Considerations such as whether the assay is qualitative, semi-quantitative or quantitative, the particular detection device and the concentration of BAP will normally determine the concentration of other reagents.

The term "labelled antibody" indicates the unique anti-BAP, highly non-cross-reactive monoclonal antibodies of the present invention that are labelled by conventional methods to form all or part of a signal generating system. Thus, the present monoclonal antibodies can be covalently bound to radioisotopes such as tritium, carbon 14, phosphorous 32, iodine 125 and iodine 131 by methods well known in the art. For example, $^{125}I$ can be introduced by procedures such as the chloramine-T procedure, enzymatically by lactoperoxidase procedure or the by the are labelled Bolton-Hunter technique. These techniques plus others are discussed in H. Uan Vunakis and J. J. Langone, Editors, *Methods in Enzymolgy*, Vol. 70, Part A, 1980. See also U.S. Pat. No. 3,646,346, issued Feb. 29, 1972, and Edwards et al., U.S. Pat. No. 4,062,733, issued Dec. 13, 1977, respectively, both of which are herein incorporated by reference, for further examples of radioactive labels.

Chromogenic labels are those compounds that absorb light in the visible ultraviolet wavelengths. Such compounds are usually dyestuffs and include quinoline dyes, triarylmethane dyes, phthaleins, insect dyes, azo dyes, anthraquimoid dyes, cyanine dyes, and phenazoxonium dyes.

Fluorogenic compounds include those which emit light in the ultraviolet or visible wavelength subsequent to irradiation by light. The fluorogens can be employed by themselves or with quencher molecules. The primary fluorogens are those of the rhodamine, fluorescein and umbelliferone families. The method of conjugation and use for these and other fluorogens can be found in the art. See, for example, J. J. Langone, H. Van Vunakis et al., *Methods in Enxymology*, Vol. 74, Part C, 1981, especially at page 3 through 105. For a representative listing of other suitable fluorogens, see Tom et al., U.S. Pat. No. 4,366,241, issued Dec. 28, 1982, especially at column 28 and 29. For further examples, see also U.S. Pat. No. 3,996,345, herein incorporated by reference.

These non-enzymatic signal systems are adequate for the present invention. However, those skilled in the art will recognize that enzyme-catalyzed signal system is in general more sensitive than a non-enzymatic system. Thus, for the instant invention, catalytic labels are the more sensitive non-radioactive labels.

Catalytic labels include known in the art and include single and dual ("channelled") enzymes such as alkaline phosphatase, horseradish peroxidase, luciferase, β-galactosidase, glucose oxidase, (lysozyme, malate dehydrogenase, glucose-6-phosphate dehydrogenase,) and the like. Examples of dual ("channeled") catalytic systems include alkaline phosphatase and glucose oxidase using glucose-6-phosphate as the initial substrate. A second example of such a dual cataivtic system is illustrated by the oxidation of glucose to hydrogen peroxide by glucose oxidase, which hydrogen peroxide would react with a leuco dye to produce a signal generator. (A further discussion of catalytic systems can be found in Tom et al., U.S. Pat. No. 4,366,241, issued Dec. 28, 1982, herein incorporated by reference. (See especially columns 27 through 40.) Also, see Weng et al., U.S. Pat. No. 4,740,468, issued Apr. 26, 1988, herein incorporated by reference, especially at columns 2 and columns 6, 7, and 8.

The procedures for coupling enzymes to the antibodies are well known in the art. Reagents used for this procedure include glutaraldelyde, p-toluene diisocyanate, various carbodiimide reagents, p-benzoquinone m-periodate, N, N$^1$-o-Phenylenedimaleimide and the like (see, for example, J. H. Kennedy et al., *Clin. Chim Acta* 70, 1 (1976)).As another aspect of the invention, any of the above devices and formats may be provided in a kit in packaged combination with predetermined amounts of reagents for use in assaying BAP. Where an enzyme is the label, the reagents will include an antibody that is highly specific for BAP as described above and will also be conjugated to the appropriate enzyme, substrate for the enzyme or precursors therefor including any additional substrates, enzymes, and cofactors and any reaction product to provide the detectable chromophore or fluorophore. The relative amount of the various reagents may be varied widely, to provide for concentrations in solution of the reagents which substantially optimize the sensitivity and specificty of the assay. The reagents can be provided as dry powders, usually lyophilized, including excipients, which on dissolution will provide for a reagent solution having the appropriate concentrations for performing the assay.

Chemiluminescent labels are also applicable. See, for example, the labels listed in C. L. Maier, U.S. Pat. No. 4,104,029, issued Aug. 1, 1978, herein incorporated by reference.

The substrates for the catalytic systems include simple chromogens and fluorogens such as para-nitrophenyl phosphate (PNPP), β-D-glucose (plus possibly a suitable redox dye), homovanillic acid, o-dianisidine, bromocresol purple powder, 4-alkyl-umbelliferone, luminol, para-dimethylaminoiophine, paramethoxylophine, AMPPD, and the like.

Depending on the nature of the label and catalytic signal producing system, one would observe the signal, by irradiating with light and observing the level of fluorescence: providing for a catalyst system to produce a dye, fluorescence, or chemiluminescence, where the dye could be observed visually or in a spectrophotometer and the fluorescence could be observed visually or in a fluorometer; or in the case of chemiluminescence or a radioactive label, by employing a radiation counter. Where the appropriate equipment is not available, it will normally be desirable to have a chromophore produced which results in a visible color. Where sophisticated equipment is involved, any of the techniques is applicable.

The monoclonal antibodies useful in the present invention are obtained by the process discussed by Milsrein and Kohler and reported in *Nature* 256, 495–497, 1975. The details of this process are well known and will not be repeated here. However, basically it involves injecting a mouse with an immunogen. (In the current case, the immunogen used is a source rich in BAP, such as a human osteosarcoma cell.) The mouse is subsequently sacrificed and cells taken from its spleen are fused with myeloma cells. The result is a hybrid cell, referred to as a "hybridoma," that reproduces in vitro. The population of hybridomas is screened and manipulated so as to isolate individual clones each of which secretes a single antibody species to the antigen. Each individual antibody species obtained in this way is the product of a single B cell from the immune animal generated in response to a specific antigenic site recognized on the immunogenic substance.

When an immunogenic substance is introduced into a living host, the host's immune system responds by producing antibodies to all the recognizable sites on the substance. This "shotgun" approach to producing antibodies to combat the invader results in the production of antibodies of differing affinities and specificities for the immunogenic substance. Accordingly, after the different hybridoma cell lines are screened to identify those that produce antibody to BAP, the antibodies produced by the individual hybridoma cell lines are preferably screened to identify those having the highest affinity for BAP stimulating their original production before selection for use in the present invention. Selection based on this criterion is believed to help provide the increased sensitivity in the immunometric assays of the present invention using monoclonal antibody compared to the polyclonal antibody used in the prior art which, at best, has an affinity for the antigen which is roughly the average of the affinities of all antibodies produced by the immune system. Preferably, the monoclonal antibody selected will have an affinity compatible with the desired sensitivity and range for the test system under consideration. Preferably the antibody will have an affinity of at least about $10^8$ liters/mole and, more preferably, an affinity of at Least about $10^9$ liters/mole.

Specifically, as an initial screen, the hybridomas from the initial fusions were screened using a "one-site" assay. In the assay, microtiter plates were coated with goat anti-mouse IgG. Culture supernatant from the initial hybridomas are added to the microtiter plates, incubated, and then washed to bind the anti-BAP monoclonal antibody indirectly to a solid support. Cross reactivity of the antibodies was checked by adding crude detergent extract of BAP (from SAOS-2 cells) or a crude butanol extract of LAP (from human liver samples), washing the solid support, then measuring the activity of the bound BAP or LAP by measuring its effect on PNPP substrate (para-nitrophenyl phosphate). Those antibodies that bound at least 2.0 times more BAP than LAP (as measured by either enzymes activity on PNPP) were grown and expanded. The hybridomas were subsequently given a definitive RIA screen for BAP vs LAP cross-reactivity. The RIA used $^{125}$I labelled BAP or LAP in a competitive assay format. A sample of hybridoma supernatant and measured amounts of labelled and unlabelled BAP or LAP were combined then incubated with a solid support coupled to sheep anti-mouse IgG. The solid support was washed and was placed in a gamma counter. Varying proportions of labelled or cold BAP or LAP were used to perform a saturation analysis for each antibody. Antibodies that were less than 20% crossreactive for LAP in the presence of BAP (as determined by the concentration of unlabeled antigen required to inhibit 50% of the binding of the labelled antigen) were selected for use in the two-site (or "sandwich") immunometric assay. It is monoclonal antibodies that are less than 20% crossreactive with LAP in the presence of BAP that are referred to in this disclosure as "highly specific for BAP, especially in the presence of LAP".

As foreshadowed above, yet another aspect of the present invention are monoclonal antibodies that are highly specific for BAP, especially in the presence of LAP. Preferred embodiments of this aspect of the invention include antibodies BA1F 419, BA1G 017, BA1G 121, BA1G 151, and BA1G 339.

The hybridomas that produce antibodies BA1B 067, BA1F 419, BA1G 017, BA1G 121, BA1G 151, and BA1G 339, which are referred to by the designation of the antibody they produce, were deposited with the American Type Culture Collection (Rockville, Md.) as follows:

| Hybridoma | Deposit Date | Accession Number |
|---|---|---|
| BA1B 067 | January 26, 1989 | HB 10004 |
| BA1F 419 | January 26, 1989 | HB 10005 |
| BA1G 017 | January 26, 1989 | HB 10002 |
| BA1G 121 | January 26, 1989 | HB 10007 |
| BA1G 151 | January 26, 1989 | HB 10003 |
| BA1G 339 | January 26, 1989 | HB 10006 |

Figure 2:
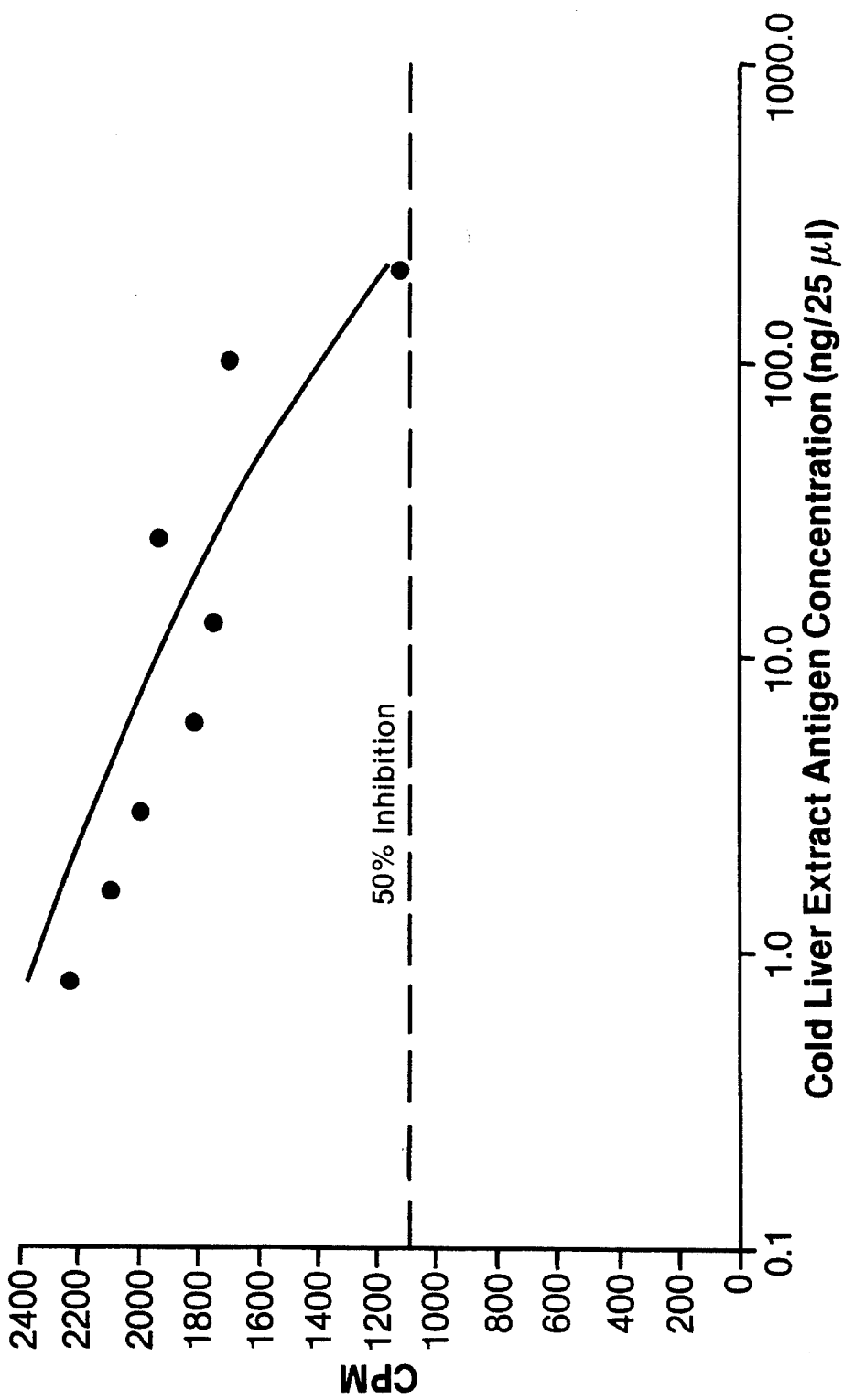
FIG. 2 depicts the simultaneous analysis of monoclonal antibody BA1G 121 using radiolabelled, purified BAP and crude, unlabelled LAP.
Figure 3:
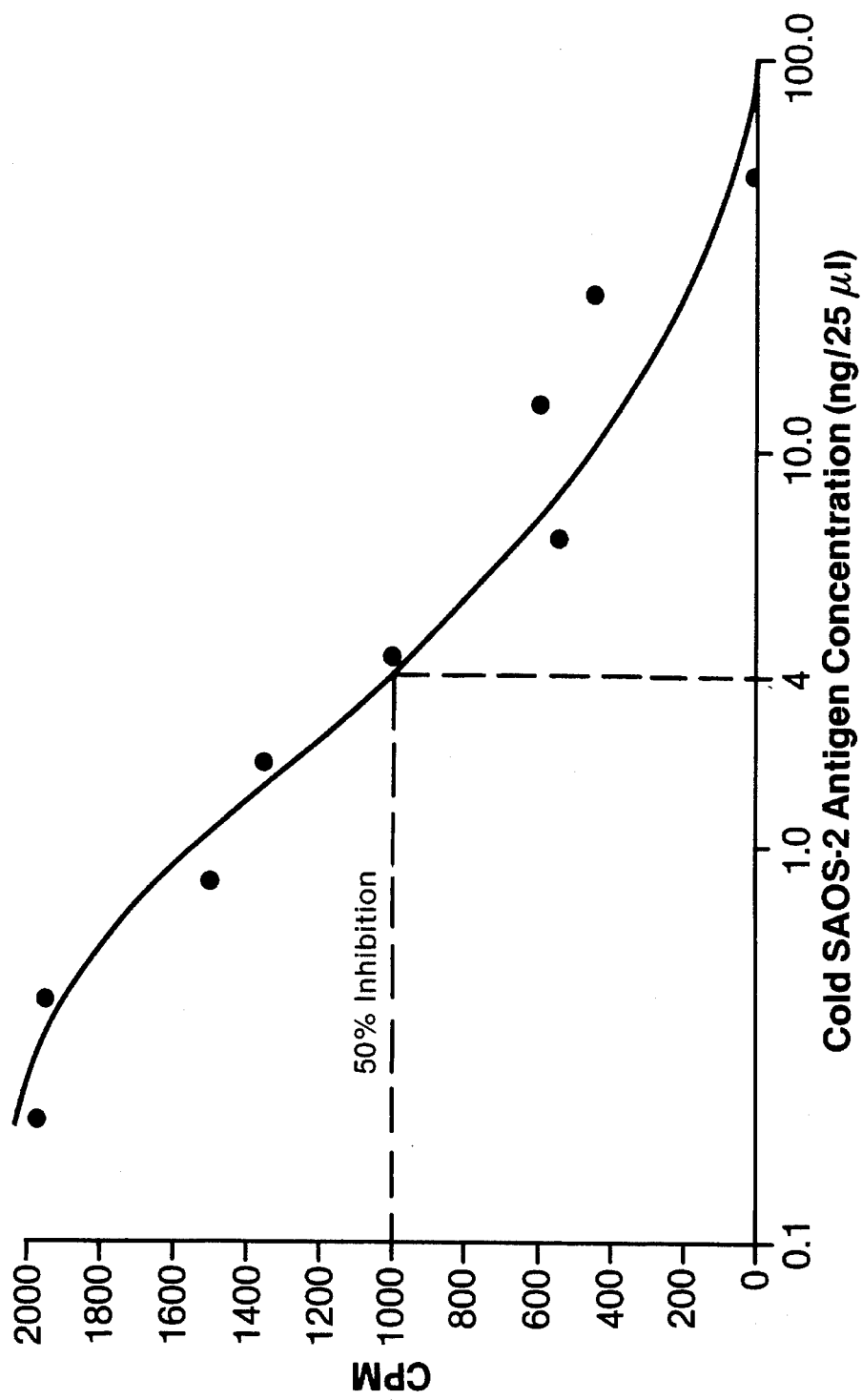
FIG. 3 is similar to FIG. 1 except that the monoclonal antibody analyzed is BA1B 067.
Figure 4:
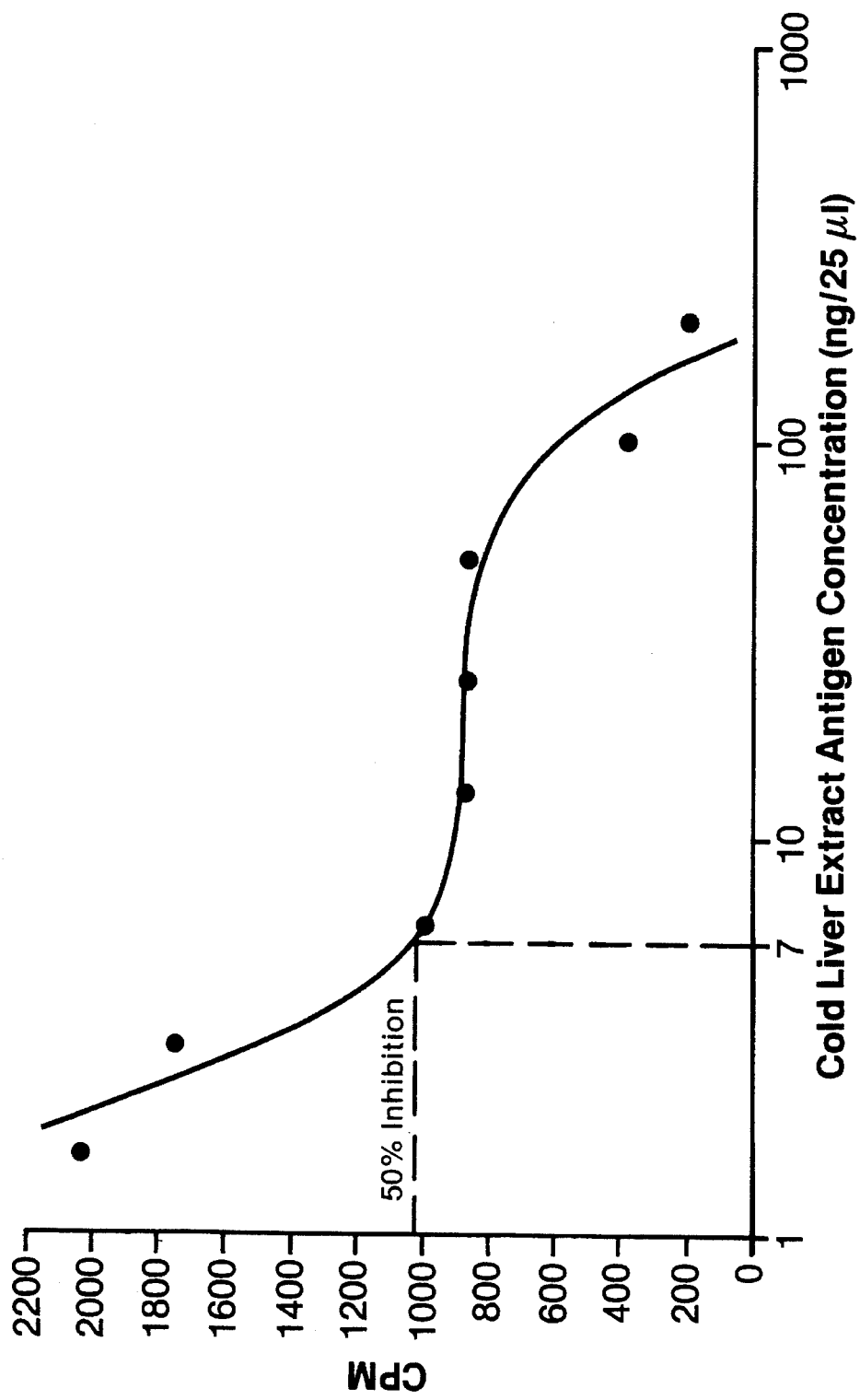
FIG. 4 is similar to FIG. 2 except that the monoclonal antibody being analyzed is BA1B 067.
Figure 5:
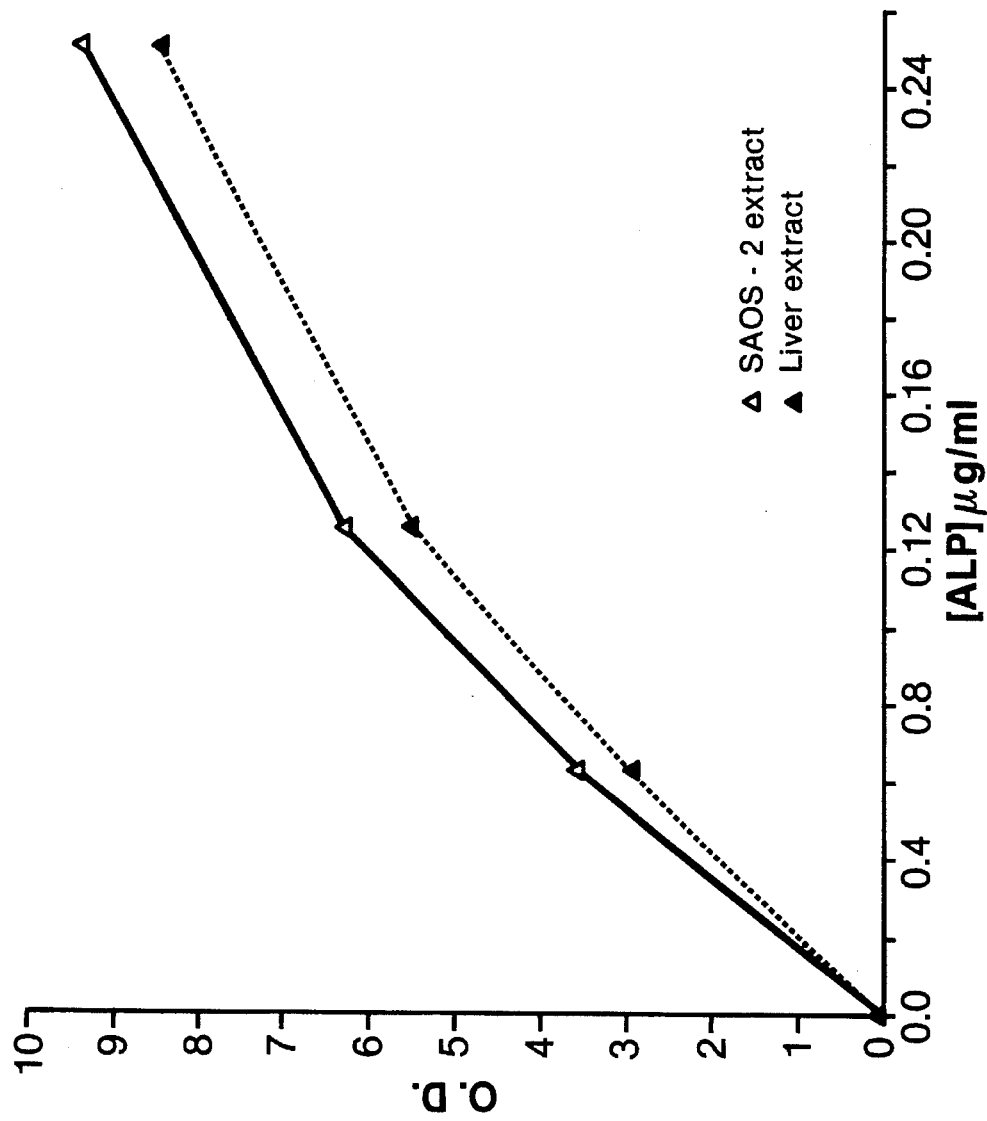
FIG. 5 depicts the dose-response curve generated with a sandwich assay employing BA1F 419 as the capture antibody, BA1B 067 as the labelled antibody, and either crude LAP or crude BAP extracts as the analyte.
Figure 6:
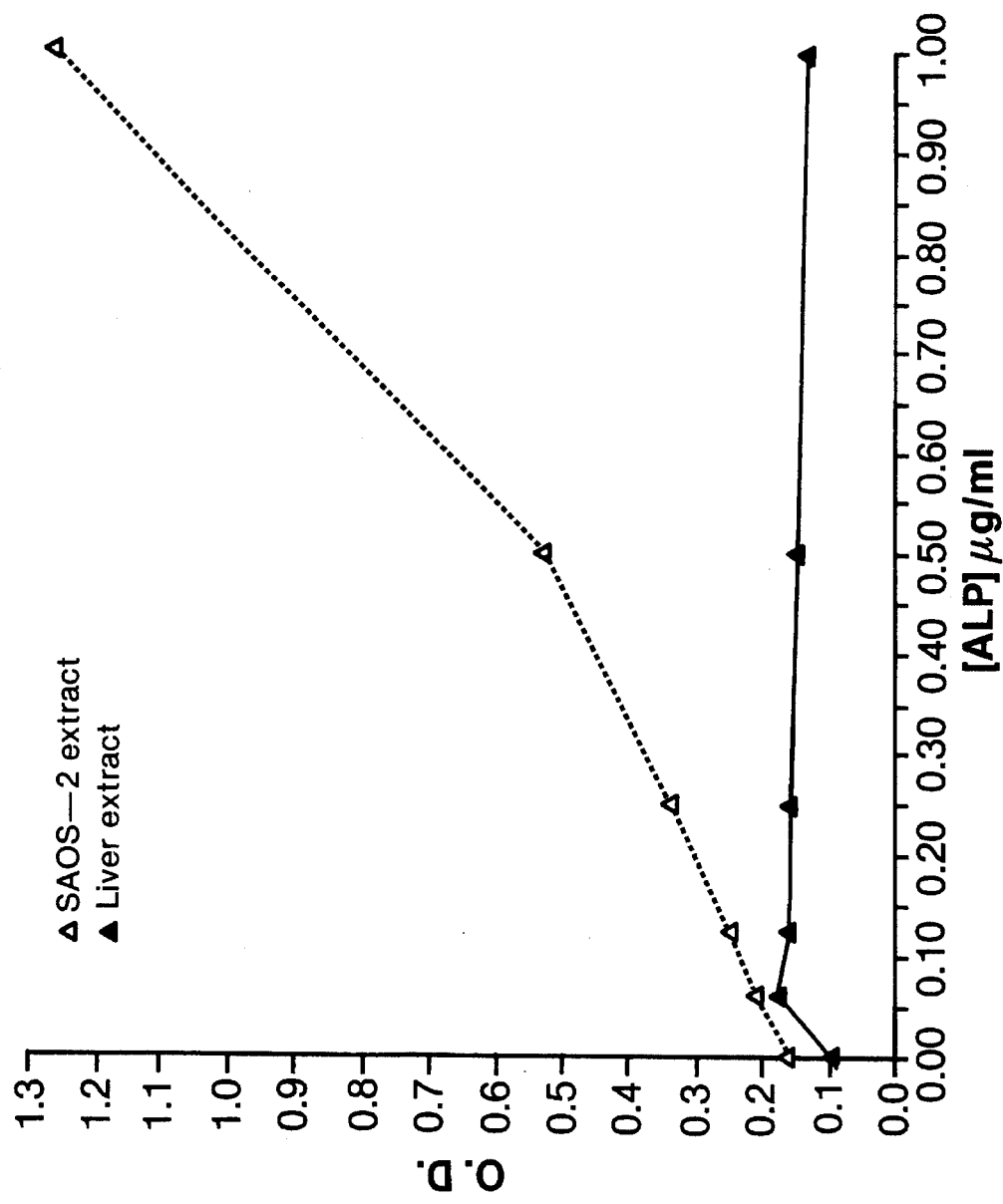
FIG. 6 is similar to FIG. 5, except that BA1G 017 is the labelled antibody.

As stated earlier in this discussion, for the two site assay of the instant invention to selectively detect BAP in the presence of LAP, the capture antibody and the labelled antibody both must be highly non crossreactive with LAP in the presence of BAP. This requirement is graphically demonstrated by FIGS. 1 through 9. FIGS. 1 and 2 show the specificity of antibody BA1G 121 for BAP over LAP. The sequential saturation analyses of these figures employed labelled BAP antigen followed by addition of cold (crude) BAP antigen (for FIG. 1) or LAP antigen (FIG. 2). The analyses demonstrated that the 50% inhibition concentration of cold antigen to differ greatly for BAP and LAP for BA1G 121, thus the antibody was specific for BAP epitopes and highly non-crossreactive with LAP epitopes. A similar set of experiments with BA1B 067 (FIGS. 3 and 4) shows the 50% inhibition level in the competitive RIA saturation analyses for BAP and LAP to be approximately the same. Thus, BA1B 067 does not have the required high specificty for BAP over LAP. Those skilled in the art would have predicted that a sandwich or two site assay using one monoclonal antibody highly specific for BAP and non-crossreactive with LAP and another monoclonal antibody specific for alkaline phosphatases in general but cross-reactive for BAP and LAP would give a highly specific assay for BAP over LAP. For instance, the highly BAP-specific monoclonal antibody could be the capture antibody bound to the solid support. Thus, the sample containing the BAP analyte (and LAP also) could be incubated and the unbound BAP, LAP and other antigens in the test solution be removed in a wash step..The (labelled) antibody that was non specific for BAP could then be incubated with the complex-containing solid support, followed by washing and the addition of chromogen, fluorogen or chemuluminescent agent if necessary. The capture antibody highly specific for BAP should, under normal circumstances, enable the assay to distinguish BAP over LAP. A sandwich assay such as this was performed, using the highly specific BA1F 419 antibody as the capture antibody and the cross-reactive BA1B 067 antibody as the labelled antibody (the saturation analysis data for BA1F 419 is given in Example 1). The results of the assays with crude BAP and crude LAP are shown in FIGS. 5 and 6. The dose response curves, set forth in FIG. 5, show no significant difference in the detection of LAP and BAP in in vitro conditions. If the same highly specific capture antibody is used but substituting a highly specific (labelled) antibody BA1G 017 the assay responds in a markedly different manner, as graphically set forth in FIG. 6. The assay essentially does not respond to a difference in the concentration of LAP, while there is a positive dose response curve for a change in BAP concentration. (The slopes of other highly specific antibodies used in conjunction with the capture antibody BA1F 419 are also set forth below in conjunction with Example 4.)

The requirement for both the capture and the labelled antibody to be highly specific for BAP especially in the presence of LAP, exists not only in sandwich assays for partially purified human samples but with human patient samples obtained in the normal ways for diagnostic purposes.

Figure 7:
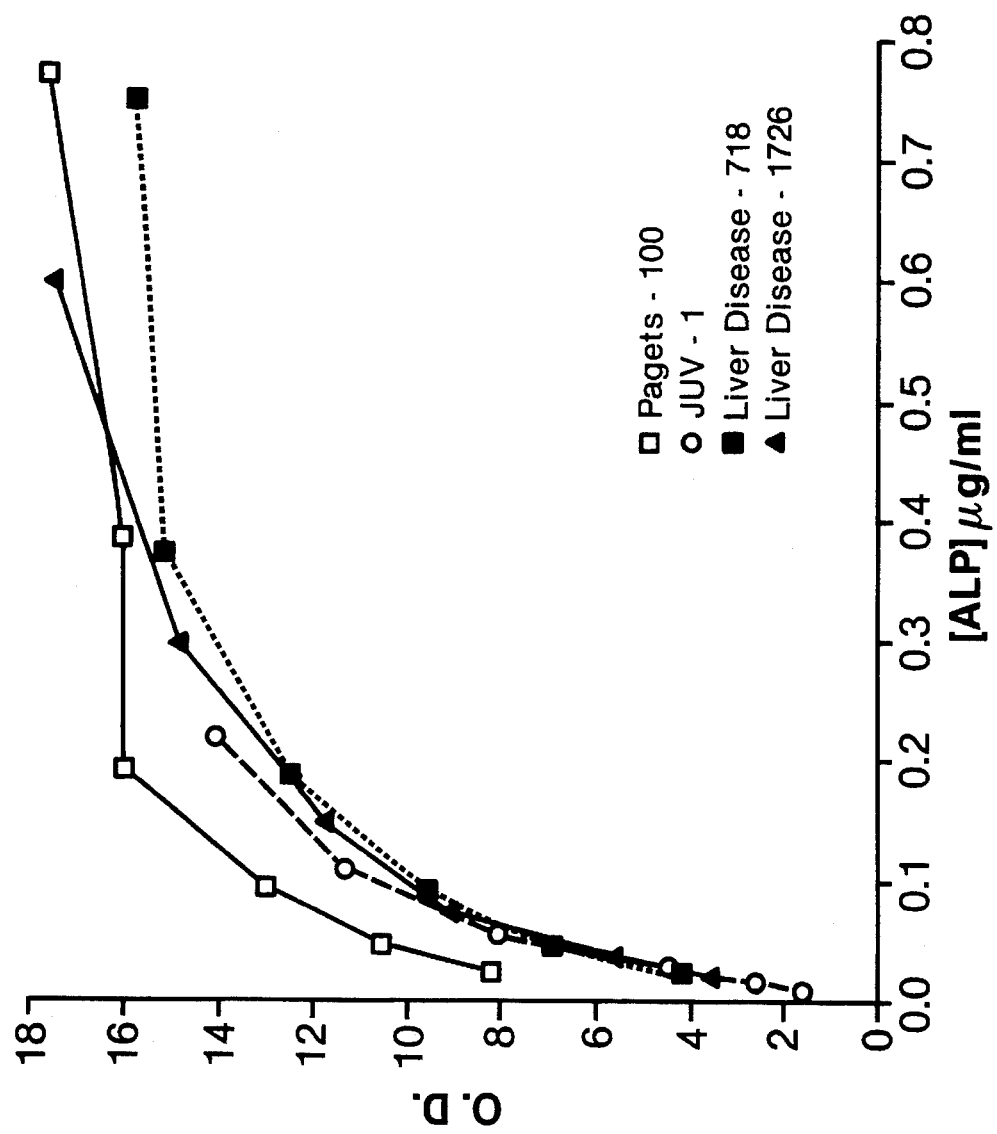
FIG. 7 depicts dose response curves for a sandwich assay analyzing human sera samples with elevated concentrations of either BAP or LAP using BA1F 419 as the capture antibody and BA1B 067 as the labelled antibody.
Figure 8:
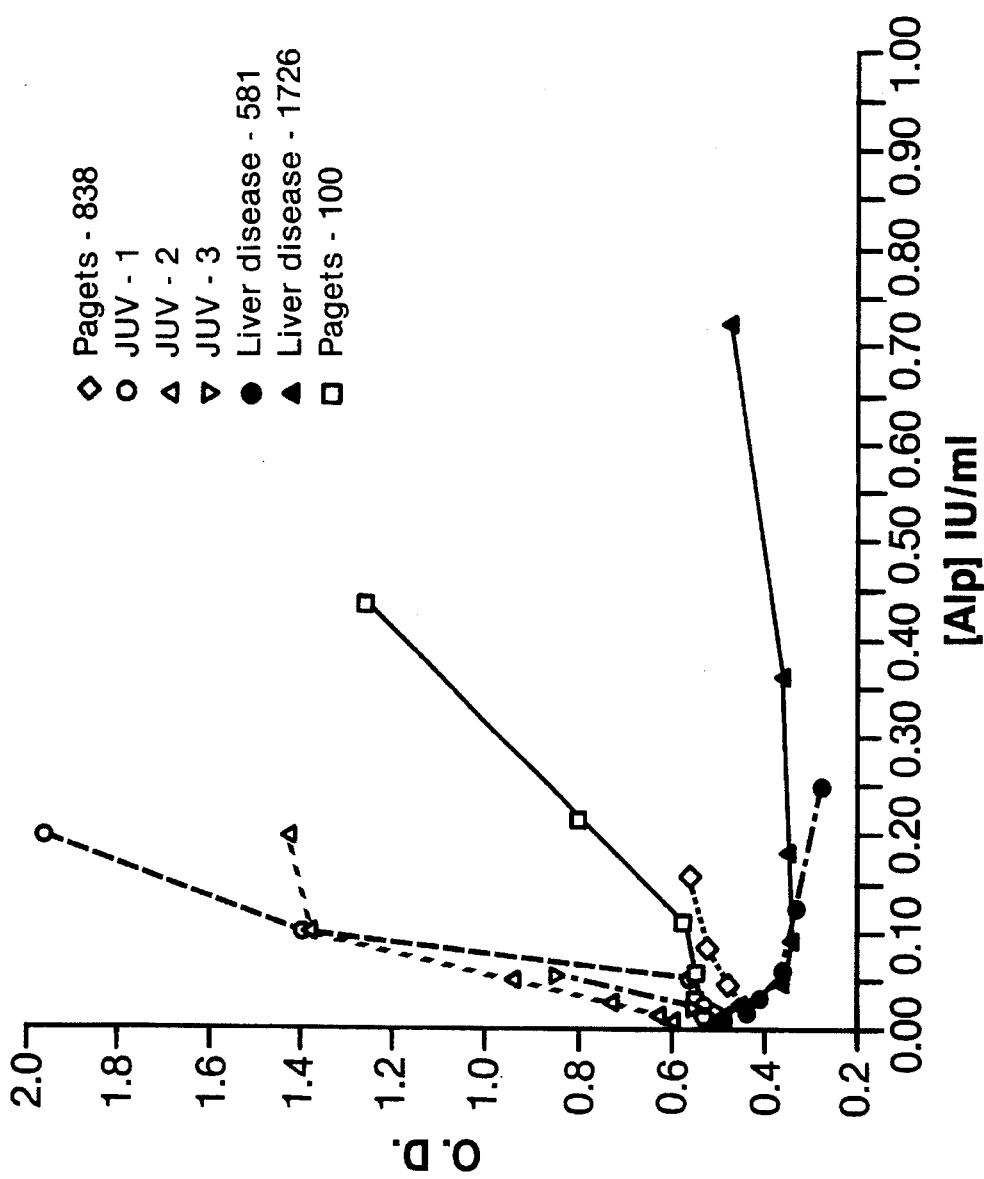
FIG. 8 is similar to FIG. 7 except that monoclonal antibody BA1G 121 is used as the labelled antibody.
Figure 9:
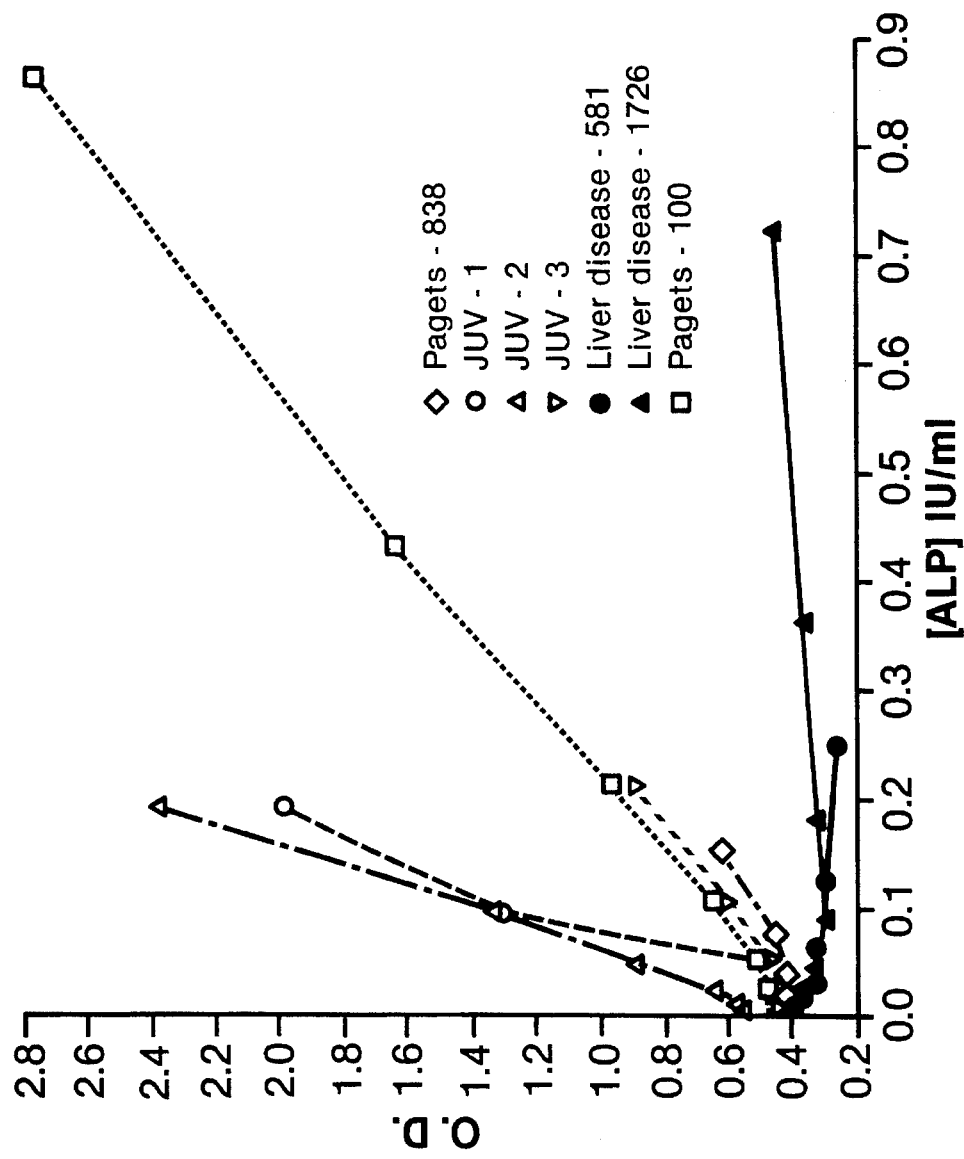
FIG. 9 is similar to FIG. 8 except that monoclonal antibody BA1G 339 is used as the labelled antibody.

FIG. 7 charts the results of a sandwich assay again employing highly specific monoclonal antibody BA1F 419 as the capture antibody and the crossreactive monoclonal antibody BA1B 067 as the labelled antibody. Little difference is seen in dose response curves in human sera taken from patients whose sera will have elevated levels of LAP (i.e., patients with various forms of liver disease) and those patients whose sera will have elevated levels of BAP (i.e., patients with Paget's Disease or healthy juvenile ("JUV- 1") patients). In contrast, FIGS. 8 and 9 set forth the results of the sandwich assay using the same highly non-crossreactive capture antibody (BA1F 419) but this time using two highly BAP-specific antibodies (BA1G 339 and BA1G 121, whose RIA data is presented below in Example 2) as labelled antibodies. The difference in dose response curves for these two assays (as depicted in FIGS. 8 and 9) over the assay depicted in FIG. 7 is dramatic. The dose response curves in FIGS. 8 and 9 show that the assays described in the graphs have a positive response to increasing concentrations of BAP-containing sere (Paget's disease patients and normal juvenile (i.e., "JUV-1", "JUV-2", and "JUV-3") patients) versus the flat response to increasing concentrations of sera containing elevated levels of LAP and normal levels BAP (i.e. patients with liver disease).

Yet another aspect of the present invention is a kit for detecting the presence or concentration of BAP, comprising a monoclonal antibody for BAP which is bound or can be bound to a solid carrier, a labelled monoclonal antibody, and a signal generating substance if required, wherein both monoclonal antibodies are highly specific for BAP, especially in the presence of LAP. Thus, the antibodies and assay formats discussed above and exemplified below can be supplied as a kit. Once again, the solid carrier can either be bound to the capture antibody at the time the reaction between the capture antibody and the BAP takes place, or the solid carrier can be coated with a substance that binds the capture antibody (e.g. sheep antimouse antibody) such that the solid carrier binds to the capture antibody after the antibody binds to the BAP antigen.

The kit can additionally contain substrate for the enzyme or the requisite precursors for the substrate, including any additional substrates, enzymes, and cofacters and any reaction partner of the enzymic product required to provide the detectable chromophore or fluorophore. In addition, other additives such as ancillary reagents may be included, for example, stabilizers, buffers, and the like. The relative amounts of the various reagents may vary widely, to provide for concentrations in solution of the reagents which substantially optimize the sensitivity and specificty of the assay.

The reagents can be provided as dry powders, usually lyophillized, including excepients, which on dissolution will provide for a reagent solution having the appropriate concentrations for performing the assay.

Preferred embodiments of the kit use combinations of the antibodies BA1F 419, BA1G 017, BA1G 121, BA1G 151, or BA1G 339 as either the capture or the labelled antibody, or alternatively where the kit uses one of these antibodies as both the capture and the labelled antibody.

Experimental

The abbreviations used in the following Procedures and Examples have the same meaning as is commonly used in the art. Thus, for example. "MEM" stands for modified Eagle's medium, "NP-40" stands for Nonidet P-40, "PBS" stands for phosphate-buffered saline, "PNPP" stands for para-nitrophenyiphosphate, "BSA" stands for bovine serum albumin, and the like. The following Procedures and Examples are set forth of specific instances of the general teaching set forth above on how to make and how to use the present invention.

Procedure 1

Purification of Human Bone Alkaline Phosphatase

BAP was extracted from the SAOS-2 human esteosarcoma cell line (ATCC#HTB 85) which were grown in complete MEM supplemented with 8% horse serum and 2% fetal calf serum. The cells were scraped from the culture flask and washed twice in PBS by centrifugation followed by incubation in an extraction buffer containing 1% NP-40 in a 0.1 M Tris-HCl buffer, pH 8.0. The cells were extracted for one hour at 25° C. with gentle stirring followed by centrifugation at 10,000 g for 15 min to remove the cellular debris.

The BAP preparations were purified by running the supernatants through an anti-alkaline phosphatase immunoaffinity column consisting of purified anti-alkaline phosohatase monoclonal antibodies (BA1B 067, an antibody that is specific for both BAP and LAP, and is obtained according to Procedure 3 below) coupled to activated agarose beads Affigel-10 Bio-Rad Laboratories, Richmond, Calif., according to the packate insert. The column was washed with extraction buffer followed by elution with buffer containing 125 mM KCl and 10 mM lysine at pH 11. Fractions were collected and assayed for alkaline phosphatase activity. Each fraction was assayed for alkaline phosphatase activity by combining 50 µl of appropriately diluted sample (i.e., anywhere between 2 through 200 times, depending on the concentration of the sample) with 100 µl of PNPP solution (1 PNPP tablet (Sigma) in 3 ml of water) in microtiter plates and measuring the rate of PNPP (substrate) turnover an 405 nm in a Vmax microtiter plane reader (Molecular Devices, Palo Alto, Calif.) in the kinetic reading mode at 25° C. One unit (U) of activity was defined as the quantity of enzyme that catalyzes the hydrolysis of 1 µmole of substrate per minute under these conditions. One unit of activity was considered to equal approximately one microgram of pure BAP (or LAP). Protein-containing fractions were also analyzed by SDS polyacrylamide gel elecnrophoresis (10–15% gradient reducing gels, Pharmacia Phast gel system, Pharmacia, Uppsala, Sweden). The electrophoretic analysis indicated a purity for BAP of greater than 95%. After electrophoretic analysis, the protein-containing fractions were incubated with sheep anti-mouse IgG (North Valley Farms, San Diego, Calif.) coupled to cyanogen bromide-activated Sepharose 4B beads (Pharmacia, Upsala, Sweden) to remove mouse IgG. The yields of BAP from the crude detergent extract were typically approximately 50%.

Procedure 2

Purification of Human Liver Alkaline Phosphatase

LAP was extracted from human liver samples by suspending the diced, washed samples in an extraction buffer consisting of 30% butanol in a buffer at pH 7.5 containing 2 mM $MgCl_2$, 0.025 mM $ZnCl_2$, 10 mM Tris-HCl, and homogenizing the mixture with a Polytron homogenizer (Brinkman Instruments, Westbury, N.Y.). The homogenate was incubated at 25° C. for 16 hr followed by 8 hr at 4° C. with gentle stirring. Centrifugation was performed at 9000 g for 30 min (Beckman Instruments, Model J2-21, Palo Alto, Calif.) and the aqueous phase was separated from the butanol phase and the pellet. The aqueous phase was clarified by centrifuging at 20,000 g for 20 min. The LAP preparations were purified and analyzed as in Procedure 1. Electrophoretic analysis as in Procedure 1 of the protein-containing fractions showed that the LAP thus obtained was greater than 90% pure. After electrophoretic analysis, the protein-containing fractions were incubated with sheep anti-mouse IgG as in Procedure 1. The yields of LAP from crude butanol extract were typically approximately 33%.

EXAMPLE 1

Production and Isolation of Monoclonal Antibodies BA1F 419, BA1G 017, BA1G 121, BA1G 151, and BA1G 339.

Balb/c and A/J mice were immunized with SAOS-2 cells which had been extracted with a Triton-X containing buffer. Mice were immunized using complete Freunds adjuvant for the initial injection followed by incomplete Freunds adjuvant at day 14. Boosts (e.g., BA1B - 1 boost, BA1F 419- 2 boosts, BA1G's - 1 boost) were repeated at 14 day intervals with PBS. Fusion of P3.653 myeloma cells and spleen cells from immunized animals were performed according to Kohler and Milsrein (1975), as modified and described in Oi and Herzenberg, *Selective Methods in Cellular Immunology*, Mishell, B. B., and Shigii, S. M., Eds., W. H. Freeman and Company, San Francisco, Chapter 17, (1980). Serum titers and initial screening of clones were done by the RIA procedure described below. Hybridomas which were identified to be secreting alkaline phosphatase reactive antibodies were grown in mouse ascites.

Alkaline phosphatase-reactive antibodies were partially purified for immunoenzymetric assays by sodium sulfate fractionation ("salt cut") of mouse ascites. The salt cut was performed by determining the amount of ascites fluid collected, and adding dropwise sufficient 25% (w/v) sodium sulfate to the ascites with mixing to give a solution wherein the concentration of salt was 18%. The salt solution is then rotated for two hours at room temperature. The solution is then spun in a JA-20 centrifuge (Beckman Instruments, Palo Alta, Calif.) at 10,000 rpm for twenty minutes. The supernatant is removed and the pellet is resuspended in the 18% salt ascites solution. The solution is stirred or shaken again at room temperature for 10 to 15 minutes, spun again at 10,000 rpm, the supernatant is removed and the pellet is resuspended in a minimum volume of IX PBS. The buffered solution is dialyzed in PBS at 4° C. overnight. A portion (10 µl) of the sample is diluted with 1X PBS (1 ml) and the concentration determined at 280 nm. (Formula: Absorbance at 280 nm divided by 1.4 (constant for mouse IgG)×dilution factor=concentration of salt cut ascites in mg/ml). No further purification is required to use the antibodies in the assay set forth below.

EXAMPLE 2

Competitive Radioimmunoassay for BAP-Specific, non-LAP Cross-reactive Monoclonal Antibodies A. Radiolabelling LAP and BAP The purified BAP and IAP enzymes from Procedures 1 and 2 were labelled with $^{125}$I using Chloramine-T to give a specific activity of approximately 18 µCi/µg of protein.

B. Radioimmunoassy (RIA)

i) Determining Antibody Titer

The general procedure for the assay entailed adding hybridoma supernatant sample (25 µl) to microtiter plate wells followed by the addition of 50 µl of 1-125 labeled, purified BAP. Sepharose 4B beads (Pharmacia, Uppsala, Sweden) coupled with cyanogen bromide (Cuatrecacas, *Methods in Enzyology, J. Bio. Chem.* 245:3059 (1970) to sheep anti-mouse IgG were added and the plates were incubated overnight at 25° C. with gentle shaking. The Sepharose beads from each plate were washed with 0.1% Tween and PBS and collected with a cell harvester on paper discs and the discs were counted in a gamma counter (Iso-Data, Rolling Meadows, Ill.). This assay was used to measure the ascites titer for anti-BAP antibodies. (The titers for clones BA1F 419, BA1G 017, BA1G 121, BA1G 151, BA1G 339 and BA1B 067 are set forth in Table 1, below).

ii) Determining Specificity for BAP in the presence of LAP

This RIA procedure was also used for (simultaneous) saturation analysis of BAP for each of the antibodies. The results of this analysis using radiolabelled BAP displaced by either unlabelled BAP or unlabelled LAP are set forth in Table 1 below and FIGS. 1 through 4 above. (In general, varying amounts of crude (unlabelled) LAP or BAP (from Procedures 1 and 2) along with fixed amount of radiolabelled BAP were used to get the results set forth above.) Saturation analysis was performed by first determining the 50% titer point of the antibody sample by the above RIA procedure. Varying amounts of crude BAP or LAP were then added to the appropriate dilution of antibody sample along with a fixed amount of purified $^{125}$I BAP tracer antigen. The rest of the procedure was as described above for the RIA. The results of the competitive assays are set forth below in Table 1 below.

TABLE 1

Concentration of Cold Antigen for 50% Inhibition

| Antibody | Reactivity | Ascites Titer (RIA) | Isotype | ng BAP | ng LAP |
|---|---|---|---|---|---|
| BA1F 419 | Non-crossreactive | 1/6,400 | IgG1 | 16.8 | >200 |
| BA1G 017 | Non-crossreactive | 1/124,000 | IgG2a | 5.0 | >100 |
| BA1G 121 | Non-crossreactive | 1/129,000 | IgG2a | 6.0 | >200 |
| BA1G 151 | Non-crossreactive | 1/256,000 | IgG2a | 8.8 | >200 |
| BA1G 339 | Non-crossreactive | 1/2,000 | IgG2a | 15.8 | >200 |
| BA1B 067 | Crossreactive | 1/256,040 | IgG2a | 4.0 | 7 |

EXAMPLE 3

"One-site" Immuno-assited Enzyme Assay

A one-site immunoenzymetric assay for the detection of BAP or LAP was performed by drying down sheep anti-mouse IgG (North Valley Farms, San Diego, Calif.) in 10 mM sodium phosphate buffer (pH 7.0) on microtiter plates overnight at 37° C. The plates were rinsed with distilled water followed by a 2 minute wash in a 0.1% Tween-20/PBS solution and then rinsed again with distilled water. Plates were blocked with a PBS solution containing 1% BSA and 0.1% Tween-20. for 30 min an 37° C. and washed as before. The plates were incubated with 100 µl of culture supernatant from Example 1 for 2 hr at 37° C., washed (as above), and then incubated with crude detergent or butanol extract of either BAP or LAP (from Procedures 1 or 2) for 1 hr at 37° C. followed by washing with distilled water. PNPP substrate (1 PNPP tablet (Sigma) in 3 ml rarer was added for 30 min and the absorbance was read at 405 nm in a Vmax microtiter plate reader.

EXAMPLE 4

Sandwich Assays Specific for Human BAP

Procedure A

Biotinylation of Anti-BAP Monoclonal Antibodies

Monoclonal antibodies BA1G 017, BA1G 121, BA1G 151, BA1G 339, and BA1B 067 (the latter for comparative purposes) were each biotinylated in the following manner. The antibody (1 mg) was dissolved in 0.2M sodium bicarbonate buffer at pH 8.2 (1 ml). To this solution was added biotin N-hydroxy-succinimide ester (120 mg). The resultant solution was incubated on a rotator at 25° C. for 1.5 hours then dialyzed against PBS for 16 hours with two changes of PBS.

Procedure B

The Sandwich Assay—Microtiter Plate

The sandwich assay was performed by drying a PBS solution of the capture antibody (BA1F 419) for this assay in a microtiter plate and washing and blocking as described above in Example 3. A solution (5 µg/ml) of biotin-labeled antibody (either BA1G 017, BA1G 121, BA1G 151, BA1G 339, or for comparison, BA1B 067) was added together with 50 µl of the various dilutions of antigen sample (from either Procedures 1 or 2 above) and the plates were incubated for 4 hours at 25° C. The antibody and antigen dilutions were made in a solution consisting of 5% non-fat dry milk (Alba), 0.01% anti-foam A emulsion (Sigma Chemical Co., St. Louis, Mo.) and 0.001% Thimerosol in PBS. The plates were washed and 50 µl of streptavidin-conjugated horseradish peroxidase (Jackson Laboratories Inc., Avondale, Pa.) (0.1 µg/ml in 0.1% Tween 20% PBS) was added for 1 hr at 25° C. The plates were washed with distilled water then incubated for 15 min with a solution of 0-Phenylenediamine substrace (Sigma). The plates were read at 490 run in a microtiter plate spectrophotometer (Bio-Tek ELISA reader, Bio-Tek instrument Co.. Burlington, Vt.) The results of assays using BA1F 419 as the capture antibody and either BA1G 017, BA1G 151, BA1G 339, or (for comparison) BA1B 067 as the labelled antibody in an in vitro assay set forth below in Table 2 and in FIGS. 5 and 6.

TABLE 2

BAP Tandem Assay: Slope of the Dose-Response Curves[1]

| Antibody | Reactivity | BAP | LAP | Ratio BAP/LAP Response |
|---|---|---|---|---|
| BA1G 017 | Non-cross reactive | 1.09 | −0.00633 | [2] |
| BA1G 151 | Non-cross reactive | 2.36 | 0.01430 | 165.0 |
| BA1G 339 | Non-cross reactive | 1.79 | 0.00587 | 305.0 |

TABLE 2-continued

BAP Tandem Assay: Slope of the Dose-Response Curves[1]

| Antibody | Reactivity | BAP | LAP | Ratio BAP/LAP Response |
|---|---|---|---|---|
| BA1B 067 | cross reactive | 36.50 | 33.10000 | 1.1 |

[1]O. D. (Abs. 490)/μg/ml total ALP
[2]Cannot be calculated, implies absolute specificity.

FIGS. 7, 8, and 9 above show the results of assays analyzing human sera expected to be rich in either BAP and LAP. BA1F 419 was again used as the capture antibody and antibodies BA1G 339 (FIG. 9) and BA1G 121 (FIG. 8) plus BA1B 067 (for comparison, FIG. 7) were used as the biotin-labelled antibodies. The procedure for these assays using human sera followed that of the above in vitro assays substituting the sera for the extracted antigen.

Procedure C

The Sandwich Assay—Bead Format

Polystyrene beads (5/16 inch diameter) were prepared by linking the antibody covalently to aminopolysterene beads using dimethyl suberimidate (DMS).

I) Polystyrene beads are first nitrated in a 100 ml round bottom flask equipped with a stirbar to which 25.0 ml of concentrated sulfuric acid ($H_2SO_4$) followed by 12.5 ml of concentrated nitric acid ($HNO_3$) is added. Chill, using an ice bath, until a temperature of 5°–10° C. is maintained for a minimum of five minutes. Add 100 polystyrene beads making sure that all beads are in thorough contact with the acid mixture. React for about 20 minutes at 5°–10° C. with gentle stirring. The temperature should not exceed 10° C.

Filter the beads using a Buchner funnel. Retain the acid mixture for disposal later. Pour the beads into cold (4°–8° C.) deionized water. Use a volume of water sufficient to completely immerse the beads. Drain the water and repeat the rinse twice more.

The beads are then aminated in a 100 ml round bottom flask equipped with a stirbar to which add 29.5 ml of concentrated hydrochloric acid (HCl) and 29.5 g of stannous chloride ($SnCl_2$) is added. The mixture should be maintained at room temperature (20°–25° C.). Add the nitrated polystyrene beads making sure that all beads are in thorough contact with the acid mixture and react for two hours. After the reduction is complete, drain the beads using a Buchner funnel into a separate acid container for later disposal. (Note: Under no circumstances should the nitration and amination acid mixtures come in contact. Contact results in an explosive reaction.) All rinses employ enough buffer/water to thoroughly immerse the beads. Rinse the beads for approximately 1 minute by immersing in 0.1 M HCl. Drain and repeat the 0.1 M HCl rinse. Rinse the beads for approximately 1 minute by immersing in deionized water. Drain and repeat the deionized water rinse. Rinse the beads for approximately 1 minute by immersing in 0.1M NaOH. Drain the beads and rinse twice more using deionized water. Store the beads protected from light in 0.20 M Sodium Phosphate, pH 7.0, 0.1% Sodium Azide at 2°–8° C.

II) The functionalized beads were treated in a solution of 0.05M DMS in 0.25M triethanolamine at pH 9.3 for 20 minutes at room temperature with gentle agitation. The beads were then washed in 0.05M sodium phosphate buffer at pH 8.0. The beads were then immersed in a solution of the same sodium phosphate buffer containing the BA1G 151 (any other antibody could be used at this point) antibody (0.05–0.1 mg/ml) am 2°–8° C. for 18–24 hours. The beads were washed in 0.1M sodium phosphate buffer that is 1.0M in sodium chloride at pH 6.0 for 1 hour followed by incubation in the same buffer that additionally contains 0.2% Tween 20 for 15–20 minutes. The beads were washed in the same buffer but without Tween 20 for 8–12 minutes followed by rinsing in deionized water with agitation for 5 minutes. The beads were blocked with 0.1% BSA (Miles Laboratories, Naperville, Ill.) in 0.05M sodium phosphate buffer at pH 7.2 for 3 hours at 53° C. with agitation at 20 minute intervals. The beads were drained and rinsed three times with 1.0M sodium chloride solution, 0.1M sodium phosphate buffer at pH 6.0, and then stored in 0.05M sodium phosphate buffer at pH 7.2 that also contains 0.1% sodium azide at 2°–8° C. for future use. (All antibodies used for the bead assay were purified by the HPLC procedure of Procedure 3).

The antibody (e.g., BA1G 151) was labelled by the Glucose Oxidase Lactoperoxidase (GOLP) iodination method using Enzymobeads (Bio-Rad, Calif.) according to the directional insert to a specific activity of approximately 7–8 μCi/μg of protein.

The antigen for calibration and validation was extracted from SAOS-2 cells and LAP was extracted from human liver as described above. The extracted antigen was diluted into a matrix consisting of 10% BSA, 0.1% sodium azide, 0.1% mannitol, 0.001% NP-40, 0.1M sodium phosphate-citrate buffer at pH 7.0. The antigen was diluted based on total alkaline phosphate activity measured as above. Calibration was typically made at 0, 0.1, 0.2, 0.4, and 0.6 Units/ml.

The assay format using the above reagents and calibrators was as follows:

A) add the sample or calibrator to the assay test tube;

B) add a solution (100 μl) of the radiolabelled antibody (diluted to give 200,000 cpm per tube) to the tubes;

C) add one bead to the tube;

D) incubate the mixture on a shaker at room temperature for 2 hours;

E) wash the bead 3 times with Tandem®-R wash reagent (Hybritech Incorporated, San Diego, Calif., a detergent solution containing 0.3% sodium azide as a preservative); and F) detect the signal present on the bead with a gamma counter.

The above bead assay constitutes a preferred embodiment of the invention. The most preferred conditions for the bead assay format used BA1G 151 as both the capture (i.e. bead) and the labelled antibody. Other combinations, such as BA1G 151 as the capture and BA1G 121 as the labelled antibody, and vice versa, and BA1G 121 as both capture and labelled antibody, work well and are preferred bead assay conditions. Other combinations of the BA1F 419, BA1G 017, BA1G 121, BA1G 151, or BA1G 339 successfully detected BAP in the bead assay format and are included within the scope of the present invention.

Procedure 3

Production of Cross-Reactive Antibody BA1B 067

Monoclonal Antibody BA1B 067 was produced along the lines of Examples 1 and 3. Initially the analysis of Example 2 was not carried out on the antibody as purified samples of BAP and LAP were to be obtained only after BA1B 067 had been produced and purified. In addition to the purification step set forth in Example 1, BA1B 067 was further purified by high pressure liquid chromatography column on a Bio-Rad HPLC instrument equipped with a TSK DEAE anion-exchange column (Bio-Rad Laboratories, Richmond, Calif.) which was eluted with a linear gradient of 20 mM Tris-HCl, pH 8.5 to 300 mmol sodium chloride, 20 mmol Tris-HCl pH 7.0. This purification was used only for affinity column manufacture and the bead assays.

We claim:

1. A process for the determination of the presence or concentration of BAP enzyme in a fluid comprising the steps:

(a) contacting a sample of the fluid with a first monoclonal antibody for BAP, wherein the first monoclonal antibody is bound to a solid carrier insoluble in the fluid, in order to form an insoluble complex between the first monoclonal antibody and BAP;

(b) separating the fluid sample containing unreacted BAP from the insoluble complex of the first monoclonal antibody and BAP;

(c) reacting a measured amount of a second monoclonal antibody to BAP which is labeled and which antibody is soluble in the fluid with the insoluble complex of the first monoclonal antibody and BAP, in order to form an insoluble complex of the first monoclonal antibody, BAP, and second monoclonal antibody;

(d) separating the solid carrier from unreacted second antibody;

(e) measuring either the amount of second antibody associated with the solid carrier or the amount of unreacted second antibody;

(f) relating the amount of second antibody measured with the amount of labeled antibody measured for a control sample prepared in accordance with steps (a) through (e), said control sample being known to be free of BAP, to determine the presence of BAP in said fluid sample, or relating the amount of labeled antibody measured for the fluid sample with the amount of labeled antibody measured for samples containing known amounts of BAP prepared in accordance with steps (a) through (e) to determine the concentration of BAP in the fluid sample;

wherein both monoclonal antibodies used are less than 20% cross-reactive with LAP in the presence of BAP.

2. A process according to claim 1, wherein the first monoclonal antibody is the product of a different cell line than the second monoclonal antibody.

3. A process according to claim 1, wherein the first and second monoclonal antibodies are the product of the same cell line.

4. A process according to claims 2 or 3 wherein the second, labelled antibody is labelled with a radioactive isotope, an enzyme, biotin, avidin, a chromogenic substance, or a fluorogenic substance.

5. A process according to claim 4, wherein the monoclonal antibodies are chosen from the group consisting of BA1F 419, BA1G 017, BA1G 121, BA1G 151, and BA1G 339 produced by the hybriodoma cell lines with ATCC Accession Numbers HB 10005, HB 10002, HB 10007, HB 10003, and HB 10006, respectively.

6. A process according to claim 5, wherein the label is the radioactive isotope $^{125}$I.

7. A process according to claim 5, wherein the label is an enzyme other than alkaline phosphatase.

8. A process according to claim 5, wherein the second, labelled antibody is labelled with biotin, and wherein the amount of labelled antibody is measured by adding a measured amount of streptavidin-conjugated enzyme label wherein the enzyme is other than an alkaline phosphatase.

9. A process of claim 1, wherein the first monoclonal antibody is bound directly or indirectly to a porous membrane.

10. A process of a claim 9, wherein the first monoclonal antibody is attached to insoluble microparticles, which microparticles in turn are bound to a porous membrane.

11. The process of claim 4, wherein the first monoclonal antibody is bound directly or indirectly to a porous membrane.

12. A process of claim 11, wherein the first monoclonal antibody is bound to microparticles, which microparticles are in turn bound to a porous membrane.

13. A process for the determination of the presence of concentration of BAP enzyme in a fluid comprising the steps:

(a) contacting a sample of the fluid with a measured amount of the first monoclonal antibody for BAP, wherein the first monoclonal antibody is labelled, in order to form a soluble complex between the first monoclonal antibody and the BAP;

(b) contacting the soluble complex with a second monoclonal antibody to BAP, which second antibody is bound to a solid carrier insoluble in the fluid with the soluble complex of the first monoclonal antibody and BAP, in order to form an insoluble complex of the first monoclonal antibody, BAP, and second antibody;

(c) separating the solid carrier from the fluid sample and unreacted first antibody;

(d) measuring either the amount of first antibody associated with the solid carrier or the amount of unreacted first antibody;

(e) relating the amount of first antibody measured with the amount of labelled antibody measured for a control sample prepared in accordance with steps (a) thru (d), said control sample being known to be free of BAP, to determine the presence of BAP in said fluid sample, or relating the amount of labelled antibody measured for the fluid sample with the amount of labelled antibody measured for samples containing known amounts of BAP prepared in accordance with steps (a) thru (d) to determine the concentration of BAP in the fluid sample;

wherein the both monoclonal antibodies are less than 20% cross-reactive with LAP in the presence of BAP.

14. A process according to claim 13, wherein the first monoclonal antibody is the product of a different cell line from the second monoclonal antibody.

15. A process according to claim 13, wherein the first and second monoclonal antibodies are a product of the same cell line.

16. A process according to claims 14 or 15 wherein the first, labelled antibody is labelled with a radioactive isotope, an enzyme, biotin, avidin, a fluorogenic substance or a chromogenic substance.

17. A process according to claim 16, wherein the monoclonal antibodies are chosen from the group consisting of BA1F 419, BA1G 017, BA1G 121, BA1G 151 and BA1G 339 produced by hybridoma cell lines with ATCC Accession Numbers HB 10005, HB 10002, HB 10007, HB 10003, and HB 10006, respectively.

18. A process according to claim 17, wherein the label is the radioactive isotope $^{125}$I.

19. A process according to claim 17, wherein the label is an enzyme other than alkaline phosphatase.

20. A process according to claim 17, wherein the first, labelled antibody is labelled with biotin, and wherein the amount of labelled antibody is measured by adding a measured amount of streptavidin-conjugated enzyme label wherein the enzyme is other than an alkaline phosphatase.

21. A process of claim 13, wherein the second monoclonal antibody is bound directly or indirectly to a porous membrane.

22. A process of a claim 21, wherein the second monoclonal antibody is attached to insoluble microparticles, which microparticles in turn are bound to a porous membrane.

23. The process of claim 16, wherein the second monoclonal antibody is bound directly or indirectly to a porous membrane.

24. A process of claim 23, wherein the second monoclonal antibody is bound to microparticles, which microparticles are in turn bound to a porous membrane.

25. A process for the determination of the presence of concentration of BAP enzyme in a fluid comprising the steps:
   (a) simultaneously contacting a sample of the fluid with a first and second monoclonal antibodies for BAP, wherein the first monoclonal antibody is bound to a solid carrier insoluble in the fluid and the second monoclonal antibody is labelled and provided in a measured amount in order to form an insoluble complex between the first monoclonal antibody and the BAP antigen;
   (b) separating the solid carrier from the fluid sample containing unreacted second antibody;
   (c) measuring either the amount of second antibody associated with the solid carrier or the amount of unreacted second antibody;
   (d) relating the amount of second antibody measured with the amount of labelled antibody measured for a control sample prepared in accordance with steps (a) thru (c), said control sample being known to be free of BAP, to determine the presence of BAP in said fluid sample, or relating the amount of labelled antibody measured for the fluid sample with the amount of labelled antibody measured for samples containing known amount of BAP prepared in accordance with steps (a) thru (c) to determine the concentration of BAP in the fluid sample;
   wherein the monoclonal antibodies used are less than 20% cross-reactive with LAP in the presence of BAP.

26. A process according to claim 25, wherein the first monoclonal antibody is the product of a different cell line than said second antibody.

27. A process according to claim 25, wherein the first and second monoclonal antibodies are the product of the same cell line.

28. A process according to claim 26 or 27 wherein the second, labelled antibody is labelled with a radioactive isotope, an enzyme, biotin, avidin, a fluorogenic substance or a chromogenic substance.

29. A process according to claim 28, wherein the monoclonal antibodies are chosen from the group consisting of BA1F 419, BA1G 017, BA1G 121, BA1G 151, or BA1G 339 produced by the hybridoma cell lines with ATCC Accession Numbers HB 10005, 10002, 10007, 10003, and 10006, respectively.

30. A process according to claim 29, wherein the label is the radioactive isotope 125I.

31. A process according to claim 29, wherein the label is an enzyme other than alkaline phosphatase.

32. A process according to claim 29, wherein the second, labelled antibody is labelled with biotin, and wherein the amount of labelled antibody is measured by adding a measured amount of streptavidin-conjugated enzyme label wherein the enzyme is other than an alkaline phosphatase.

33. A process of claim 25, wherein the first monoclonal antibody is bound directly or indirectly to a porous membrane.

34. A process of a claim 33, wherein the first monoclonal antibody is attached to insoluble microparticles, which microparticles in turn are bound to a porous membrane.

35. The process of claim 28, wherein the first monoclonal antibody is bound directly or indirectly to a porous membrane.

36. A process of claim 35, wherein the first monoclonal antibody is bound to microparticles, which microparticles are in turn bound to a porous membrane.

37. A kit for detecting the presence or concentration of BAP, comprising a monoclonal antibody for BAP which is bound or can be bound to a solid carrier a labelled monoclonal antibody, and a signal generating substance if required, wherein both monoclonal antibodies are less than 20% cross-reactive with LAP in the presence of BAP.

* * * * *